(12) United States Patent
Briant et al.

(10) Patent No.: US 9,095,670 B2
(45) Date of Patent: *Aug. 4, 2015

(54) INHALATION DEVICE AND METHOD OF DISPENSING MEDICAMENT

(75) Inventors: John Briant, Hertfordshire (GB); Patrick Campbell, Hertfordshire (GB); Charles Cooke, Hertfordshire (GB); Christopher Groombridge, Hertfordshire (GB); James Daniel John, Hertfordshire (GB); Nicholas Smartt, Hertfordshire (GB); William Bakewell, Hertfordshire (GB); Nicholas Harrison, Hertfordshire (GB); Orest Lastow, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 1087 days.

This patent is subject to a terminal disclaimer.

(21) Appl. No.: 13/129,393

(22) PCT Filed: Oct. 7, 2009

(86) PCT No.: PCT/SE2009/051110
§ 371 (c)(1),
(2), (4) Date: Feb. 13, 2012

(87) PCT Pub. No.: WO2010/042033
PCT Pub. Date: Apr. 15, 2010

(65) Prior Publication Data
US 2012/0125330 A1    May 24, 2012

Related U.S. Application Data

(60) Provisional application No. 61/103,606, filed on Oct. 8, 2008.

(51) Int. Cl.
*A61M 15/00*    (2006.01)

(52) U.S. Cl.
CPC ....... *A61M 15/0091* (2013.01); *A61M 15/0003* (2014.02); *A61M 15/0026* (2014.02);
(Continued)

(58) Field of Classification Search
CPC .............. A61J 1/035; A61M 15/0045; A61M 15/0061; A61M 15/0033; A61M 15/0051; A61M 15/0048; A61M 15/0003; A61M 15/0043; A61M 15/0091; A61M 15/0026; B65D 83/0463; B65D 75/327
USPC .............. 128/200.24, 203.15, 203.19, 203.21; 222/83
See application file for complete search history.

(56) References Cited

U.S. PATENT DOCUMENTS 6,651,341 B1    11/2003 Myrman et al.
6,941,947 B2    9/2005 Young et al.
(Continued)

FOREIGN PATENT DOCUMENTS

AU    740035    10/2001
GB    2 447 560 A    9/2008
(Continued)

OTHER PUBLICATIONS

International Patent Application No. PCT/SE2009/051110: International Search Report and Written Opinion, dated Jan. 22, 2010 (14 pages).
(Continued)

*Primary Examiner* — Annette Dixon
(74) *Attorney, Agent, or Firm* — Finnegan, Henderson, Farabow, Garrett & Dunner LLP

(57) ABSTRACT

An inhaler, including a base having at least one air-tight, foil-sealed cavity containing medicament is disclosed. An actuator is engagable with a separating element attached to the foil, the actuator having an energized position in which it is biased towards an unloaded position so as to cause the separating element and attached foil to be moved away from the cavity. A latch has a first position, in which it latches the actuator in said energized position, wherein the latch is at least partly arranged in a flow path such that an inhalation flow through the flow path affects the latch to move from the first position to the second position. A method of dispensing a medicament from a sealed cavity inside an inhaler is also disclosed.

15 Claims, 8 Drawing Sheets

(52) U.S. Cl.
CPC ....... *A61M15/0043* (2014.02); *A61M 15/0045* (2013.01); *A61M 15/0048* (2014.02); *A61M 2202/064* (2013.01); *A61M 2205/073* (2013.01)

(56) References Cited

U.S. PATENT DOCUMENTS

| | | | |
|---|---|---|---|
| 8,393,322 B2 * | 3/2013 | Lastow | 128/203.21 |
| 8,397,718 B2 * | 3/2013 | Lastow | 128/203.21 |
| 2003/0172927 A1 | 9/2003 | Young et al. | |
| 2004/0206773 A1 * | 10/2004 | Ede et al. | 222/83 |
| 2005/0172963 A1 | 8/2005 | Allan et al. | |
| 2008/0092887 A1 | 4/2008 | Hodson et al. | |
| 2011/0253138 A1 * | 10/2011 | Briant et al. | 128/203.12 |
| 2012/0048272 A1 * | 3/2012 | Briant et al. | 128/203.21 |
| 2013/0220320 A1 * | 8/2013 | Lastow | 128/203.21 |

FOREIGN PATENT DOCUMENTS

| | | |
|---|---|---|
| JP | 06-502095 A | 3/1994 |
| JP | 09-504455 A | 5/1997 |
| JP | 2001-511402 A | 8/2001 |
| JP | 2005-502440 A | 1/2005 |
| WO | WO 92/08509 A1 | 5/1992 |
| WO | WO 95/11715 A1 | 5/1995 |
| WO | WO 97/25086 A2 | 7/1997 |
| WO | WO 99/06092 A1 | 2/1999 |
| WO | WO 99/27987 A1 | 6/1999 |
| WO | WO 99/36116 A1 | 7/1999 |
| WO | WO 00/53248 A1 | 9/2000 |
| WO | WO 01/26720 A1 | 4/2001 |
| WO | WO 01/72605 A1 | 10/2001 |
| WO | WO 03/024514 A1 | 3/2003 |
| WO | WO 2005/002654 A2 | 1/2005 |
| WO | WO 2005/030305 A1 | 4/2005 |
| WO | WO 2006/000758 A1 | 1/2006 |
| WO | WO 2006/118527 A1 | 11/2006 |
| WO | WO 2008/010765 A1 | 1/2008 |
| WO | WO 2008/101992 A1 | 8/2008 |
| WO | WO 2009/008001 A2 | 1/2009 |
| WO | WO 2009/008832 A1 | 1/2009 |

OTHER PUBLICATIONS

Supplementary European Search Report issued in European Application No. 09819487.1 on Mar. 3, 2014 (3 pages).

* cited by examiner

INHALATION DEVICE AND METHOD OF DISPENSING MEDICAMENT

This is a U.S. National Phase Application of PCT/SE2009/051110, filed on Oct. 7, 2009, which claims the benefit of priority to U.S. Provisional Application No. 61/103,606, filed on Oct. 8, 2008, all of which are incorporated herein by reference.

TECHNICAL FIELD

The present invention relates to an inhaler comprising a base having at least one sealed cavity containing medicament. The invention also relates to a method of dispensing a medicament from a sealed cavity inside an inhaler.

BACKGROUND OF THE INVENTION

There are different types of inhalers on the market. A pressurized Metered Dose Inhaler (pMDI) releases a fixed dose of substance in aerosol form. A powder inhaler generally releases a dose of powdered substance entrained in an air stream. In a powder inhaler the powder may be provided in a bulk container of the inhaler from which doses of powder are metered for dispensing. As an alternative to a bulk container, powder inhalers may comprise a single compartment or a plurality of compartments for containing one or more discrete doses of powdered substance. Such compartments may take the form of sealed blisters in a blister pack, a cavities-containing strip joined to a sealing strip or other suitable forms.

EP 1 220 698 discloses an inhaler for medicament in powder form. The medicament is arranged in the inhaler in a number of enclosures. When the airflow in the inhaler reaches a certain threshold value, a breath-activated activating means causes an elongated hollow body to pierce the enclosure so that the medicament is accessed.

U.S. Pat. No. 6,651,341 discloses a foil-cutting device for opening a foil protecting a dose of medical powder carried by a dosing cassette for an inhaler. When a user inhales through the inhaler the foil-cutter opens the foil for access to a pre-metered powder dose.

When a foil is cut or pierced there is a risk that small fragments of the foil material are detached and become inhaled by the user.

WO99/36116 discloses a dry powder inhaler which, in one embodiment, has a foil flap covering a medicament cavity. The foil flap is said to be lifted by an inhalation airflow, thereby exposing the medicament which is then said to be drawn along by the air flow. This embodiment is shown in FIG. 10. There is no disclosure of the foil being glued or welded over the cavity or of the foil creating an air-tight or moisture-tight seal.

SUMMARY OF THE INVENTION

An object of the present invention is to reduce the risk of foil material forming a cavity seal becoming inhaled by the user. This and other objects, which will become apparent in the following, are accomplished by the inhaler and the method defined in the accompanied claims.

The present invention is based on the insight that the risk of foil material from a cavity seal becoming inhaled with the medicament may be reduced by removing (as opposed to cutting or piercing) at least that portion of a foil which covers and is sealingly fastened over the opening of a medicament-containing cavity. A potential problem with removing the foil is that the cavity contents are then vulnerable to being displaced, e.g. if the inhaler is inverted before the user inhales. This situation may be compared, e.g. with penetration of the cavity using a hollow member through which the contents of the cavity are subsequently inhaled; in this case the tube and remaining foil around the tube may prevent the conents of the cavity becoming inadvertently displaced from the cavity.

This potential problem is addressed by breath actuation, since if the lid is lifted simultaneously with a breath being taken, there is no opportunity for the powder to be displaced from the cavity prior to inhalation. In fact, an inhaler design described herein has been tested in the inverted orientation and found to perform substantially as well as in the normal orientation with the cavity mouth facing upwards.

According to a first aspect of the invention, an inhaler is provided. The inhaler comprises a base having at least one sealed cavity containing medicament, a foil portion comprising two sides, one side being attached to the base and sealing the cavity in an air-tight manner, a separating element which is attached to the other side of the foil portion for separating the foil portion from the cavity, an opening mechanism comprising an actuator which is engagable with the separating element, the actuator having an energized position in which it is biased towards an unloaded position, wherein during movement from the energized position to the unloaded position the actuator causes the separating element to be moved away from the cavity, and a latch having a first position, in which it latches the actuator in said energized position, and a second position, in which it allows the actuator to be in said unloaded position, wherein the latch is at least partly arranged in a flow path such that an inhalation flow through the flow path affects the latch to move from the first position to the second position.

Thus, rather than making a hole through the foil to access the medicament in the cavity, the foil is moved away, e.g. snapped-off, peeled-off or lifted, from the cavity. The removed foil, being attached to the separating element, may even function as a flow path-defining element.

It should be noted that in this application terms such as "upper", "lower", "above", "below" are used to describe the internal relationship between elements of the inhaler. Therefore, in this application the cavity is regarded as being placed "below" the foil portion, while the separating element is regarded as being placed "above" the foil portion, regardless of how the inhaler as a whole is held or turned by the user. Similarly, "horizontal" means a direction located in the plane of the foil portion or any plane parallel to the plane of the foil portion, and "vertical" means any direction perpendicular to such planes. Thus, a vertical line may intersect the cavity, the foil portion and the separating element.

The separating element and the actuator may be designed in various ways. The separating element may have structural features such as one or more dogs, protrusions, indentations, flanges, hooks, channels etc. which the actuator may engage to provide a pushing force from below or a pulling force from above or lateral heaving or lifting etc. The actuator may perform various courses of motion for engaging the separating element, such as radial, rotational or tangential motions.

According to at least one example embodiment of the invention, the actuator comprises a pivotable lever comprising an engagement portion for temporarily engaging the separating element, the engagement portion being nearer the cavity when in said energized position than when in said unloaded position. The engagement portion is thus first lowered towards the base and then raised towards the unloaded position to affect the separating element with a heaving or lifting force. The engagement portion may, for instance, have a pair of jaws that grip a mating projecting portion of the separating element. Another alternative would be for the engagement portion to have a dog which is inserted into a mating forked grip of the separating element.

According to at least one example embodiment of the invention, the actuator comprises an energizable spring for providing the actuator in the energized position. Thus, the actuator can be regarded as spring-loaded. The energizable spring may, for instance, be in the form of a coil spring or a torsion spring. In the case of the actuator comprising an energizable spring in combination with a lever or other relatively non-deformable feature, a force may be exerted on the lever against the resisting force of the energizable spring, thereby providing the actuator in an energized position. However, the lever may also rest without any force against the spring (or even be spaced from the spring), wherein only the spring is caused to be energized (actuator in energized position). As the energized spring is released it will affect (e.g. hit) the lever with the released spring-force, and the lever will in turn engage the separating element (actuator in unloaded position). Another alternative is to enable the energizable spring to directly engage with the separating element without any other force-transferring elements in-between.

According to at least one example embodiment, the inhaler comprises an outlet cover movable for alternatingly closing and opening an outlet of the inhaler, such as a mouthpiece or a nasal adaptor. A pusher is connected to the outlet cover. Upon one of said closing or opening movements of the outlet cover, the connected pusher moves to push the actuator from the unloaded position to the energized position. For instance, after inhalation when a user closes the outlet cover so as to cover the outlet until the next time he/she will inhale, the closing motion will affect the actuator to be arranged in its energized (ready) position. When the user later opens the outlet cover, the inhaler is already primed and the medicament becomes dispensed by an airflow caused by the inhalation effort of the user. An alternative would be to arrange for the actuator to be energized when the user opens the outlet cover.

The pusher may comprise a protrusion, such as a ramp or a curved wall on a moving body, and may have portions which successively come (or roll) into contact with the actuator to push it to its energized position. The movement of the pusher may suitably be a rotational movement although other directions, such as linear, are conceivable. The connection between the outlet cover and the pusher may suitably extend through one or more apertures in the inhaler housing.

According to at least one example embodiment, the latch is biased towards its first position. The extent of the biased is suitably balanced against the expected airflow inducible by a user's inhalation. Thus, when an airflow exceeds a certain threshold the biasing force is overcome and the latch is moved to its second position. When the airflow drops under the threshold, the latch may return to its biased first position, however, there may be provided mechanisms for temporarily counteracting such return motion if other parts of the inhaler should move before latching takes place. Eventually, the latch will be allowed to move to the first position for latching the actuator when the actuator is moved to its energized position.

According to at least one example embodiment, the latch comprises a first element and a second element, the first element being connected to the actuator. The second element has a supporting position, in which it immobilizes the first element, thereby preventing the actuator from moving to the unloaded position, and a non-supporting position, in which the first element is enabled to move, thereby allowing the biased actuator to move to the unloaded position. The second element is movable to the non-supporting position in response to the inhalation flow.

According to at least one example embodiment, the second element is biased towards its supporting position. The biasing force may be attained by a spring or other mechanical memory. An alternative, although orientation-dependent, would be taking advantage of gravitation for biasing the second element towards its supporting position.

There are various conceivable motions for the first element. For instance, the first element may be slidably connected to the actuator. Another alternative is rotatably connected, which is reflected in at least one example embodiment, wherein the first element comprises an elongated prop having a first end portion which is pivotable around an axis and a second end portion adapted to be supported by the second element. The pivot axis may be an axle forming part of or being connected to the actuator.

Similarly, there are various conceivable motions for the second element. The second element may be slidably arranged within the inhaler housing, wherein a spring extending from the inhaler housing would urge the second element to slide to its supporting position. In another alternative, which is reflected in at least one example embodiment, the second element (e.g. designed as a rocker) is pivotable around an axis, wherein in response to the inhalation flow the second element is pivoted to allow the first element (e.g. a prop) to fall off its support.

Although the inventive principle could be applied in a single dose inhaler, it is suitably implemented in a multi-dose inhaler having pre-metered doses of powdered medicament. Further, although the inventive principle could be applied in a inhaler wherein the multiple doses are provided in linearly arranged cavities, an annular or circular configuration may be a suitable alternative.

According to at least one example embodiment, said base comprises a rotatable disk provided with a circumferentially-oriented sequence of cavities, each cavity being sealed by a respective foil portion, each foil portion being attached to a respective separating element, wherein upon rotation of the disk the separating element next in turn is presented to the actuator. The rotatable disk may be connected to a separate manually operable lever. An alternative is to connect the rotation of the disk to the movement of the outlet cover. Thus, in either the course of opening or closing the outlet cover, the disk is rotated, thereby indexing the inhaler one step to the next dose. For instance, in an embodiment wherein the closing of the outlet cover causes the actuator to move to its energized position, the rotatable disk may also be moved (indexed) as a result of said closing.

In a multi-dose inhaler, the foil portions may be provided as one foil and, optionally, the foil portions may be defined by perforations or other material weakenings for facilitating removal of a foil portion from the cavity when the associated separating element is moved away from the base. As an alternative to a single foil, the foil portions may be applied in the form of individual patches. The foil portions may be attached to the base and the separating elements by welding, gluing or other suitable method. It should be noted that the terms "foil" and "foil portion" are not limited to a single material layer. On the contrary a foil or foil portion may comprise a plurality of layers. For instance, foil may comprise a metal layer which is coated with lacquer or polymer layer on one or both sides in any suitable combination in order to provide the desired stiffness, attachment capability, etc.

In order to separate a foil portion from the cavity it is sealing, the foil portion should be appropriately attached to its associated separating element. According to at least one example embodiment of the invention, the attachment force between the separating element and the respective associated foil portion is larger than the attachment force between the base and the foil portion, whereby movement of such a separating element away from its associated cavity causes the associated foil portion to become separated from the base.

Suitably, the contact area between a foil portion and its associated attached separating element is dimensioned in such way that no ruptured flow-obstructing foil parts will remain after the separation has occurred. In other words, the flow path downstream and upstream of the cavity opening should be free from any obstructing fringes of foil. Suitably, on the base, the flow path upstream and downstream of the cavity opening is completely foil free after the separation has occurred. This may be accomplished by designing the separating element with longer (or equal) extension in the flow path direction than that of the foil portion. Since the foil portion extends across the cavity opening in order to seal the cavity, the attached separating element should also extend at least across the cavity opening. As mentioned previously, the foil portions may form part of one covering foil provided with perforations or weakenings which define the foil portions. Such perforations would be present between the cavity openings, and when the foil portions are ruptured at those perforations or weakenings any fringes would be located laterally of the cavity viewed from a flow direction perspective, and consequently no obstructing fringes would be present upstream or downstream of the cavity.

There are various ways to obtain a larger attachment force at the separating element/foil portion interface than at the foil portion/base interface. According to at least one example embodiment of the invention, the contact surface between a separating element and its associated foil portion is larger than the contact surface between that foil portion and the base. In other words the separating element/foil portion interface is larger than the foil portion/base interface. If the separating element covers the entire foil portion, then the contact surface will automatically be larger between the separating element and the foil portion than the contact surface between the foil portion and the base, because the piece of the foil portion located directly above the cavity opening is not attached to anything and only the surrounding area of the foil is attached to the base.

Another way to obtain different attachment forces is considered in at least one other example embodiment of the invention. The foil portions may comprise a first coating layer to which the base is attached and a second coating layer to which the separating elements are attached, wherein the tensile strength of the second coating layer is larger than the tensile strength of the first coating layer. The layers can provide different bonding properties, e.g. welds of different types of material, or glues of different types or amounts, or any combination thereof.

Other ways to obtain the difference in attachment forces could be to provide the separating element with specially designed geometric features, e.g. grooves into which the foil may be attached or other features that e.g. pierce the foil to create a firm grip.

Although the foil portion may be folded into grooves of the separating element or otherwise curved around the separating element e.g. to increase the attachment area, the foil portion may suitably just be flat, i.e. only extending in a single plane parallel to the base. This enables a simple assembling of the separating elements to the foil portions. When they have become assembled the foil may be attached to the base. An alternative would be to first attach the foil portions to the base, and then attach the separating elements onto the respective foil portions.

Suitably, the stiffness of the separating elements is substantially larger than the stiffness of the foil portions, wherein the separating elements enable the foil portions to perform a rigid body motion, and may thus become lifted or snapped off the base rather than peeled off.

Although the above exemplified embodiments have discussed one cavity having one associated separating element, an alternative would be to have two cavities having one common associated separating element. For instance, if two incompatible drug components are to be inhaled essentially simultaneously, they are suitably provided in two separate cavities. The two cavities may be covered and sealed by one common foil portion (or one foil portion each), which in turn is attached to a common associated separating element extending across both cavities. Thus, when the separating element is moved away from the cavity, it will bring along the foil portion, uncovering both cavities from which the drug components can be entrained in an inhalation flow. The cavities could either be located in series in the base, i.e. one cavity being downstream of the other one, or they could be located in parallel, i.e. the inhalation flow reaches the cavities essentially simultaneously.

According to a second aspect of the invention, a method of dispensing a medicament from a foil-sealed cavity inside an inhaler is provided. The method comprises providing an airflow through the inhaler to activate the opening of the sealed cavity, opening the sealed cavity in response to said airflow by removing at least that area of the foil which is in register with the cavity opening, and dispensing the medicament entrained by the airflow.

Thus, by removing the entire portion of the foil which covers the cavity opening (i.e. the spatial area surrounded by the rim of the cavity) and, optionally, also foil portions which are attached to the base portions surrounding the cavity opening, there will be no remaining fragments of foil material over the cavity opening. Although the foil portion is removed, it may be maintained substantially intact, e.g. by using a separating element as exemplified in the first aspect of the invention.

The opening of the sealed cavity may, according to at least one example embodiment, be breath triggered. Thus, when the user inhales the airflow is induced causing the opening of the sealed cavity. An alternative, would be a manually activated air flow, e.g. by pushing a piston or the like.

According to at least one example embodiment of the invention, the act of opening the sealed cavity comprises lifting the foil from the cavity. A conceivable alternative would be to peel off the foil.

It should be understood that the method of the second aspect of the invention encompasses and may be implemented with any embodiments or any features described in connection with the inhaler of the first aspect of the invention, as long as those embodiments or features are compatible with the method of the second aspect.

The inhaler may contain various active ingredients. The active ingredient may be selected from any therapeutic or diagnostic agent. For example, the active ingredient may be an antiallergic, a bronchodilator (e.g. a beta2-adrenoceptor agonist or a muscarinic antagonist), a bronchoconstrictor, a pulmonary lung surfactant, an analgesic, an antibiotic, a mast cell inhibitor, an antihistamine, an anti-inflammatory, an anti-neoplastic, an anaesthetic, an anti-tubercular, an imaging agent, a cardiovascular agent, an enzyme, a steroid, genetic material, a viral vector, an antisense agent, a protein, a peptide, a non-steroidal glucocorticoid Receptor (GR Receptor) agonist, an antioxidant, a chemokine antagonist (e.g. a CCR1 antagonist), a corticosteroid, a CRTh2 antagonist, a DP1 antagonist, an Histone Deacetylase Inducer, an IKK2 inhibitor, a COX inhibitor, a lipoxygenase inhibitor, a leukotriene receptor antagonist, an MPO inhibitor, a p38 inhibitor, a PDE inhibitor, a PPARγ agonist, a protease inhibitor, a statin, a thromboxane antagonist, a vasodilator, an ENAC blocker (Epithelial Sodium-channel blocker) and combinations thereof.

Examples of specific active ingredients that can be incorporated in the inhaler include (i) antioxidants:—Allopurinol, Erdosteine, Mannitol, N-acetyl cysteine choline ester, N-acetyl cysteine ethyl ester, N-Acetylcysteine, N-Acetylcysteine amide and Niacin;

(ii) chemokine antagonists:—BX471 ((2R)-1-[[2-[(aminocarbonyl)amino]-4-chlorophenoxy]acetyl]-4-[(4-fluorophenyl)methyl]-2-methylpiperazine monohydrochloride), CCX634, N-{2-[((2S)-3-{[1-(4-chlorobenzyl)piperidin-4-yl]amino}-2-hydroxy-2-methylpropyl)oxy]-4-hydroxyphenyl}acetamide (see WO 2003/051839), and 2-{2-Chloro-5-{[(2S)-3-(5-chloro-1'H,3H-spiro[1-benzofuran-2,4'-piperidin]-1'-yl)-2-hydroxypropyl]oxy}-4-[(methylamino)carbonyl]phenoxy}-2-methylpropanoic acid (see WO 2008/010765), 656933 (N-(2-bromophenyl)-N'-(4-cyano-1H-1,2,3-benzotriazol-7-yl)urea), 766994 (4-({[({[(2R)-4-(3,4-dichlorobenzyl)morpholin-2-yl]methyl}amino)carbonyl]-amino}methyl)benzamide), CCX-282, CCX-915, Cyanovirin N, E-921, INCB-003284, NCB-9471, Maraviroc, MLN-3701, MLN-3897, T-487 (N-{1-[3-(4-ethoxyphenyl)-4-oxo-3,4-dihydropyrido[2,3-d]pyrimidin-2-yl]ethyl}-N-(pyridin-3-ylmethyl)-2-[4-(trifluoromethoxy)phenyl]acetamide) and Vicriviroc (iii) Corticosteroids: —Alclometasone dipropionate, Amelometasone, Beclomethasone dipropionate, Budesonide, Butixocort propionate, Ciclesonide, Clobetasol propionate, Desisobutyrylciclesonide, Etiprednol dicloacetate, Fluocinolone acetonide, Fluticasone Furoate, Fluticasone propionate, Loteprednol etabonate (topical) and Mometasone furoate.

(iv) DP1 antagonisits:—L888839 and MK0525;

(v) Histone deacetylase inducers:—ADC4022, Aminophylline, a Methylxanthine or Theophylline;

(vi) IKK2 inhibitors:—2-{[2-(2-Methylamino-pyrimidin-4-yl)-1H-indole-5-carbonyl]-amino}-3-(phenyl-pyridin-2-yl-amino)-propionic acid;

(vii) COX inhibitors:—Celecoxib, Diclofenac sodium, Etodolac, Ibuprofen, Indomethacin, Meloxicam, Nimesulide, OC1768, OC2125, OC2184, OC499, OCD9101, Parecoxib sodium, Piceatannol, Piroxicam, Rofecoxib and Valdecoxib;

(viii) Lipoxygenase inhibitors:—Ajulemic acid, Darbufelone, Darbufelone mesilate, Dexibuprofen lysine (monohydrate), Etalocib sodium, Licofelone, Linazolast, Lonapalene, Masoprocol, MN-001, Tepoxalin, UCB-35440, Veliflapon, ZD-2138, ZD-4007 and Zileuton ((±)-1-(1-Benzo[b]thien-2-ylethyl)-1-hydroxyurea);

(ix) Leukotriene receptor antagonists:—Ablukast, Iralukast (CGP 45715A), Montelukast, Montelukast sodium, Ontazolast, Pranlukast, Pranlukast hydrate (mono Na salt), Verlukast (MK-679) and Zafirlukast;

(x) MPO Inhibitors:—Hydroxamic acid derivative (N-(4-chloro-2-methyl-phenyl)-4-phenyl-4-[[(4-propan-2-ylphenyl)sulfonylamino]methyl]piperidine-1-carboxamide), Piceatannol and Resveratrol;

(xi) Beta2-adrenoceptor agonists:—metaproterenol, isoproterenol, isoprenaline, albuterol, salbutamol (e.g. as sulphate), formoterol (e.g. as fumarate), salmeterol (e.g. as xinafoate), terbutaline, orciprenaline, bitolterol (e.g. as mesylate), pirbuterol, indacaterol, salmeterol (e.g. as xinafoate), bambuterol (e.g. as hydrochloride), carmoterol, indacaterol (CAS no 312753-06-3; QAB-149), formanilide derivatives e.g. 3-(4-{[6-({(2R)-2-[3-(formylamino)-4-hydroxyphenyl]-2-hydroxyethyl}amino) hexyl]oxy}-butyl)-benzenesulfonamide; 3-(4-{[6-({(2R)-2-hydroxy-2-[4-hydroxy-3-(hydroxy-methyl)phenyl]ethyl}amino)-hexyl]oxy}butyl) benzenesulfonamide; GSK 159797, GSK 159802, GSK 597901, GSK 642444, GSK 678007; and a compound selected from N-[2-(Diethylamino)ethyl]-N-(2-{[2-(4-hydroxy-2-oxo-2,3-dihydro-1,3-benzothiazol-7-yl) ethyl]amino}ethyl)-3-[2-(1-naphthyl)ethoxy]propanamide, N-[2-(Diethylamino)ethyl]-N-(2-{[2-(4-hydroxy-2-oxo-2,3-dihydro-1,3-benzothiazol-7-yl) ethyl]amino}ethyl)-3-[2-(3-chlorophenyl)ethoxy] propanamide, 7-[(1R)-2-({2-[(3-{[2-(2-Chlorophenyl) ethyl]amino}propyl)thio]ethyl}amino)-1-hydroxyethyl]-4-hydroxy-1,3-benzothiazol-2(3H)-one, and N-Cyclohexyl-N$^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide or a pharmaceutically acceptable salt thereof (e.g. wherein the counter ion is hydrochloride (for example a monohydrochloride or a dihydrochloride), hydrobromide (for example a monohydrobromide or a dihydrobromide), fumarate, methanesulphonate, ethanesulphonate, benzenesulphonate, 2,5-dichlorobenzenesulphonate, p-toluenesulphonate, napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), D-mandelate, L-mandelate, cinnamate or benzoate.)

(xii) Muscarinic antagonists:—Aclidinium bromide, Glycopyrrolate (such as R,R—, R,S—, S,R—, or S,S-glycopyrronium bromide), Oxitropium bromide, Pirenzepine, telenzepine, Tiotropium bromide, 3(R)-1-phenethyl-3-(9H-xanthene-9-carbonyloxy)-1-azoniabicyclo[2.2.2]octane bromide, (3R)-3-[(2S)-2-cyclopentyl-2-hydroxy-2-thien-2-ylacetoxy]-1-(2-phenoxyethyl)-1-azoniabicyclo[2.2.2]actane bromide, a quaternary salt (such as [2-((R)-Cyclohexyl-hydroxy-phenyl-methyl)-oxazol-5-ylmethyl]-dimethyl-(3-phenoxy-propyl)-ammonium salt, [2-(4-Chloro-benzyloxy)-ethyl]-[2-((R)-cyclohexyl-hydroxy-phenyl-methyl)-oxazol-5-ylmethyl]-dimethyl-ammonium salt and (R)-1-[2-(4-Fluoro-phenyl)-ethyl]-3-((S)-2-phenyl-2-piperidin-1-yl-propionyloxy)-1-azonia-bicyclo [2.2.2]octane salt wherein the counter-ion is, for example, chloride, bromide, sulfate, methanesulfonate, benzenesulfonate (besylate), toluenesulfonate (tosylate), napthalenebissulfonate (napadisylate or hemi-napadisylate), phosphate, acetate, citrate, lactate, tartrate, mesylate, maleate, fumarate or succinate)

(xiii) p38 Inhibitors:—681323, 856553, AMG548 (2-[[(2S)-2-amino-3-phenylpropyl]amino]-3-methyl-5-(2-naphthalenyl)-6-(4-pyridinyl)-4(3H)-pyrimidinone), Array-797, AZD6703, Doramapimod, KC-706, PH 797804, R1503, SC-80036, SCIO469, 6-chloro-5-[[(2S, 5R)-4-[(4-fluorophenyl)methyl]-2,5-domethyl-1-piperazinyl]carbonyl]-N,N,1-trimethyl-α-oxo-1H-indole-3-acetamide, VX702 and VX745 (5-(2,6-dichlorophenyl)-2-(phenylthio)-6H-pyrimido[1,6-b]pyridazin-6-one);

(xiv) PDE Inhibitors:—256066, Arofylline (3-(4-chlorophenyl)-3,7-dihydro-1-propyl-1H-Purine-2,6-dione), AWD 12-281 (N-(3,5-dichloro-4-pyridinyl)-1-[(4-fluorophenyl)methyl]-5-hydroxy-α-oxo-1H-indole-3-acetamide), BAY19-8004 (Bayer), CDC-801 (Calgene), Celgene compound ((βR)-β-(3,4-dimethoxyphenyl)-1,3-dihydro-1-oxo-2H-isoindole-2-propanamide), Cilomilast (cis-4-cyano-4-[3-(cyclopentyloxy)-4-methoxyphenyl]-cyclohexanecarboxylic acid), 2-(3,5-dichloro-4-pyridinyl)-1-(7-methoxyspiro[1,3-benzodioxole-2,1'-cyclopentan]-4-yl)ethanone (CAS number 185406-34-2)), (2-(3,4-difluorophenoxy)-5-fluoro-N-[cis-4-[(2-hydroxy-5-methylbenzoyl)amino]cyclohexyl]-)-3-pyridinecarboxamide), (2-(3,4-difluorophenoxy)-5-fluoro-N-[cis-4-[[2-hydroxy-5-(hydroxymethyl)benzoyl]amino]cyclohexyl]-3-pyridinecarboxamide,), CT2820, GPD-1116, Ibudilast, IC 485, KF 31334, KW-4490, Lirimilast ([2-(2,4-dichlorobenzoyl)-6-[(methylsulfonyl)oxy]-3-benzofuranyl]-urea), (N-cyclopropyl-1,4-dihydro-4-oxo-1-[3-(3-pyridinylethynyl)phenyl]-)-1,8-naphthyridine-3-carboxamide), (N-(3,5-dichloro-4-pyridinyl)-4-(difluoromethoxy)-8-[(methylsulfonyl)amino]-1-dibenzofurancarboxamide), ONO6126, ORG 20241 (4-(3,4-dimethoxyphenyl)-N-hydroxy+2-thiazolecarboximidamide), PD189659/PD168787 (Parke-Davis), Pentoxifylline (3,7-dihydro-3,7-dimethyl-1-(5-oxohexyl)-)-1H-purine-2,6-dione), compound (5-fluoro-N-[4-[(2-hydroxy-4-methyl-benzoyl)amino]cyclohexyl]-2-(thian-4-yloxy)pyridine-3-carboxamide), Piclamilast (3-(cyclopentyloxy)-N-(3,5-dichloro-4-pyridinyl)-4-methoxy-benzamide), PLX-369 (WO 2006026754), Roflumilast (3-(cyclopropylmethoxy)-N-(3,5-dichloro-4-pyridinyl)-4-(difluoromethoxy)benzamide), SCH 351591 (N-(3,5-dichloro-1-oxido-4-pyridinyl)-8-methoxy-2-(trifluoromethyl)-5-quinolinecarboxamide), SelCID™ CC-10004 (Calgene), T-440 (Tanabe), Tetomilast (6-[2-(3,4-diethoxyphenyl)-4-thiazolyl]-2-pyridinecarboxylic acid), Tofimilast (9-cyclopentyl-7-ethyl-6,9-dihydro-3-(2-thienyl)-5H-pyrazolo[3,4-c]-1,2,4-triazolo[4,3-a]pyridine), TPI 1100, UCB 101333-3 (N,2-dicyclopropyl-6-(hexahydro-1H-azepin-1-yl)-5-methyl-4-pyrimidinamine), V-11294A (Napp), VM554/VM565 (Vernalis), and Zardaverine (6-[4-(difluoromethoxy)-3-methoxyphenyl]-3(2H)-pyridazinone).

(xv) PDE5 Inhibitors:—Gamma-glutamyl[s-(2-iodobenzyl)cysteinyl]glycine, Tadalafil, Vardenafil, sildenafil, 4-phenyl-methylamino-6-chloro-2-(1-imidazolyl)-quinazoline, 4-phenyl-methylamino-6-chloro-2-(3-pyridyl)-quinazoline, 1,3-dimethyl-6-(2-propoxy-5-methanesulphonylamidophenyl)-1,5-dihydropyrazolo[3,4-d]pyrimidin-4-one and 1-cyclopentyl-3-ethyl-6-(3-ethoxy-4-pyridyl)-pyrazolo[3,4-d]pyrimidin-4-one;

(xvi) PPARγ agonists:—Pioglitazone, Pioglitazone hydrochloride, Rosiglitazone Maleate, Rosiglitazone Maleate ((−)-enantiomer, free base), Rosiglitazone maleate/Metformin hydrochloride and Tesaglitizar;

(xvii) Protease Inhibitors:—Alpha1-antitrypsin proteinase Inhibitor, EPI-HNE4, UT-77, ZD-0892, DPC-333, Sch-709156 and Doxycycline;

(xviii) Statins:—Atorvastatin, Lovastatin, Pravastatin, Rosuvastatin and Simvastatin (xix) Thromboxane Antagonists: Ramatroban and Seratrodast;

(xx) Vasodilators:—A-306552, Ambrisentan, Avosentan, BMS-248360, BMS-346567, BMS-465149, BMS-509701, Bosentan, BSF-302146 (Ambrisentan), Calcitonin Gene-related Peptide, Daglutril, Darusentan, Fandosentan potassium, Fasudil, Iloprost, KC-12615 (Daglutril), KC-12792 2AB (Daglutril), Liposomal treprostinil, PS-433540, Sitaxsentan sodium, Sodium Ferulate, TBC-11241 (Sitaxsentan), TBC-3214 (N-(2-acetyl-4,6-dimethylphenyl)-3-[[(4-chloro-3-methyl-5-isoxazolyl)amino]sulfonyl]-2-thiophenecarboxamide), TBC-3711, Trapidil, Treprostinil diethanolamine and Treprostinil sodium;

(xxi) ENACs:—Amiloride, Benzamil, Triamterene, 552-02, PSA14984, PSA25569, PSA23682 and AER002.

The inhaler may contain a combination of two or more active ingredients, for example a combination of two or more of the specific active ingredients listed in (i) to (xxi) herein above.

In one embodiment the inhaler contains an active ingredient selected from mometasone, ipratropium bromide, tiotropium and salts thereof, salemeterol, fluticasone propionate, beclomethasone dipropionate, reproterol, clenbuterol, rofleponide and salts, nedocromil, sodium cromoglycate, flunisolide, budesonide, formoterol fumarate dihydrate, terbutaline, terbutaline sulphate, salbutamol base and sulphate, fenoterol, 3-[2-(4-Hydroxy-2-oxo-3H-1,3-benzothiazol-7-yl)ethylamino]-N-[2-[2-(4-methylphenyl)ethoxy]ethyl]propane-sulphonamide, hydrochloride, indacaterol, aclidinium bromide, N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide or a pharmaceutically acceptable salt thereof (e.g. dihydrobromide); N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide or a pharmaceutically acceptable salt thereof (e.g. di-D-mandelate); a [2-(4-Chloro-benzyloxy)-ethyl]-[2-((R)-cyclohexyl-hydroxy-phenyl-methyl)-oxazol-5-ylmethyl]-dimethyl-ammonium salt (e.g. hemi-naphthalene-1,5-disulfonate); a (R)-1-[2-(4-Fluoro-phenyl)-ethyl]-3-((S)-2-phenyl-2-piperidin-1-yl-propionyloxy)-1-azonia-bicyclo[2.2.2]octane salt (e.g. bromide or toluenesulfonate); or a combination of any two or more thereof.

Specific combinations of active ingredients which may be incorporated in the inhaler include:—

(a) formoterol (e.g. as fumarate) and budesonide;
(b) formoterol (e.g. as fumarate) and fluticasone;
(c) N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide or a pharmaceutically acceptable salt thereof (e.g. dihydrobromide) and a [2-(4-Chloro-benzyloxy)-ethyl]-[2-((R)-cyclohexyl-hydroxy-phenyl-methyl)-oxazol-5-yl-methyl]-dimethyl-ammonium salt (e.g. hemi-naphthalene-1,5-disulfonate);
(d) N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide or a pharmaceutically acceptable salt thereof (e.g. dihydrobromide) and a (R)-1-[2-(4-Fluoro-phenyl)-ethyl]-3-((S)-2-phenyl-2-piperidin-1-yl-propionyloxy)-1-azonia-bicyclo[2.2.2]octane salt (e.g. bromide or toluenesulfonate);

(e) N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide or a pharmaceutically acceptable salt thereof (e.g. di-D-mandelate) and [2-(4-Chloro-benzyloxy)-ethyl]-[2-((R)-cyclohexyl-hydroxy-phenyl-methyl)-oxazol-5-ylmethyl]-dimethyl-ammonium salt (e.g. hemi-naphthalene-1,5-disulfonate);

(f) N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide or a pharmaceutically acceptable salt thereof (e.g. di-D-mandelate) and a (R)-1-[2-(4-Fluoro-phenyl)-ethyl]-3-((S)-2-phenyl-2-piperidin-1-yl-propionyloxy)-1-azonia-bicyclo[2.2.2]octane salt (e.g. bromide or toluenesulfonate).

DETAILED DESCRIPTION OF THE DRAWINGS

Figure 1:
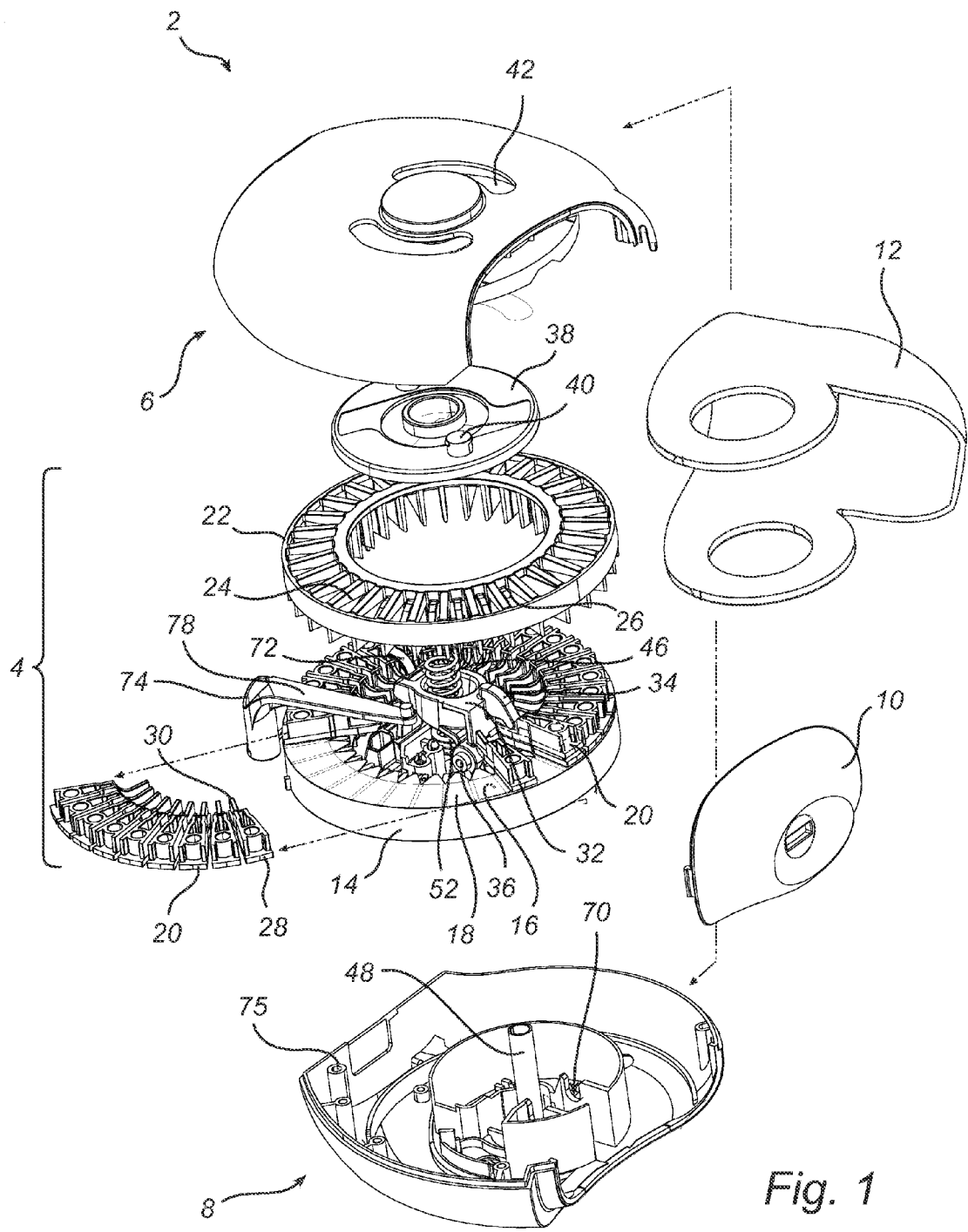
FIG. 1 is an exploded view of an inhaler according to at least one example embodiment of the invention.

FIG. 1 is an exploded view of an inhaler 2 according to at least one example embodiment of the invention. The inhaler 2 comprises a dose dispensing assembly 4 having a general disk configuration, an upper housing portion 6, a lower housing portion 8, an outlet herein represented in the form of a mouthpiece 10, and an outlet cover 12.

The dose dispensing assembly 4 comprises a circular base 14 which has a plurality of sequentially arranged cavities 16 along the circular extension of the base. The cavities 16 can be provided with medicament, such as in dry powder form, and are sealed by foil portions 18, thus providing sealed compartments. The foil portions 18 are either part of one common foil or provided as separate patches. In the shown example, perforations have been provided to define the foil portions 18 and to facilitate separation from the base 14. Above each cavity 16, a respective associated separating element 20 is attached to the upper side of the foil portion 18. The separating elements 20 are attached by any suitable type of bonding, welding, gluing, etc. to the respective foil portions 18. Upwards movement or lifting of a separating element 20 causes the attached foil portion 18 to become separated from the cavity 16.

A circular guide structure 22 is provided above the separating elements 20. The guide structure 22 comprises a plurality of guide sections 24 divided by vertically extending walls, each guide section 24 being associated with a respective separating element 20. When a separating element 20 is lifted from the cavities-holding base 14, the associated guide section 24 will guide the upwards movement of the separating element 20. Each guide section 24 is provided with a counteracting element, such as a blade spring 26. After a separating element 20 has been lifted and medicament in the opened cavity 16 has been entrained in the inhalation airflow and the separating element 20 has returned to the base 14, the blade spring 26 will keep the lifted separating element 20 in contact with the base 14 to cover the cavity 16. This will make it difficult for any remaining powder to exit the covered used cavity 16, thus reducing the risk of dose variation which could occur if such remaining powder would be entrained in a following inhalation. It also reduces the risk of remaining powder exiting the cavity 16 and jamming mechanical components in the inhaler or the risk of the separating element creating a rattling noise which would be undesirable for the user. The vertical walls dividing the circular guide structure 22 into guide sections 24 function as lateral flow path defining elements. Thus, an inhalation airflow is prevented from deviating sideways once it reaches the cavity area of the base 14 and will be led to the mouthpiece 10. An alternative would be to have shorter vertical walls, in which case neighbouring separating elements 20 could have the function of lateral flow path defining elements.

Each separating element 20 has a base-covering portion 28 which is in register with a respective cavity 16 in the base. Additionally, each separating element 20 has a centrally projecting portion 30. An opening mechanism comprising an actuator 32 for lifting the separating elements 20 is provided. The actuator is herein represented in the form of a pivotable lever provided with jaws 34 for gripping the centrally projecting portions 30 of the separating elements 20. The actuator 32 has an energized position (FIGS. 2 and 6) in which the jaws 34 are in a lowered position and, after pivoting about a pivot axel 36, an unloaded position (FIGS. 3 and 7) in which the jaws 34 are in a raised position. The actuator 32 with its jaws 34 is only pivotable around the horizontal axel 36 and will thus remain facing the mouthpiece 12 during operation of the inhaler 2.

Returning to FIG. 1, a generally disk-shaped insert 38 is provided under the upper housing portion 6. The upper side of the insert 38 is provided with two pegs 40. The pegs 40 extend upwardly through respective arcuate openings 42 in the upper housing portion 6 and are connected to the outlet cover 12. As the outlet cover 12 is rotated, the pegs 40 will through the arcuate openings 42 transmit the motion to the insert 38 which will also rotate. The underside of the insert 38 is provided with a first force transmitting member, herein illustrated in the form of a cam 44 (see FIG. 4), which will convert the rotating motion to a linear force affecting the jaws 34 of the actuator 32 in order to return the actuator 32 from its unloaded position to its energized position. As the cam 44 comes into contact with the jaws 34 of the actuator 32 (see FIG. 5), the actuator 32 will be moved radially towards the separating element 20 and will rotate around its pivot axel 36. Also, the jaws 34 will drop down to the primed or energized position of the actuator 32 (see FIG. 2). The lowering of the jaws 34 will be against the force of a coil spring 46 which is biased to raise the jaws 34 to the unloaded position. The coil spring 46 is wound around a post 48 projecting upwardly from the lower housing portion 8.

Figure 4:
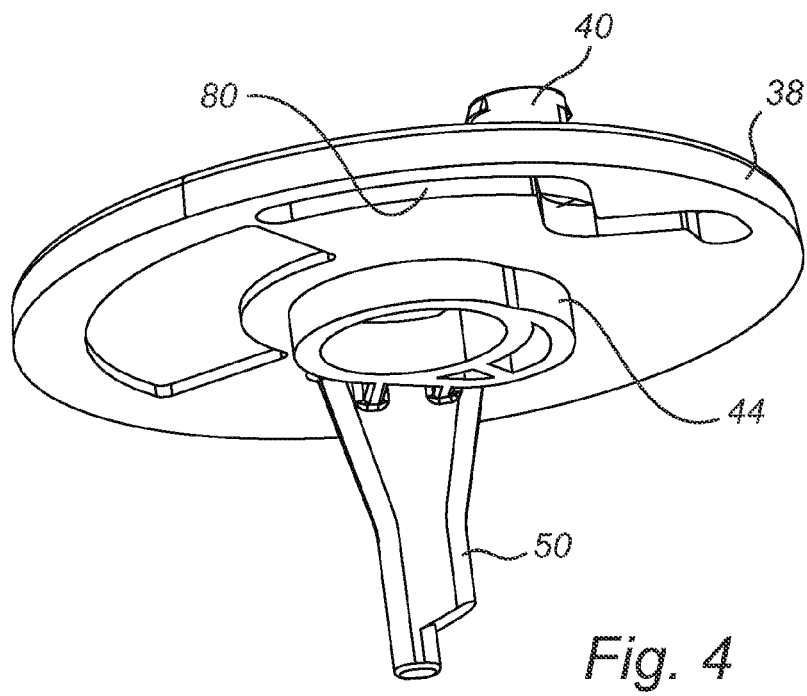
FIGS. 4 to 8 and 11 illustrate various details of the inhaler.
Figure 6:
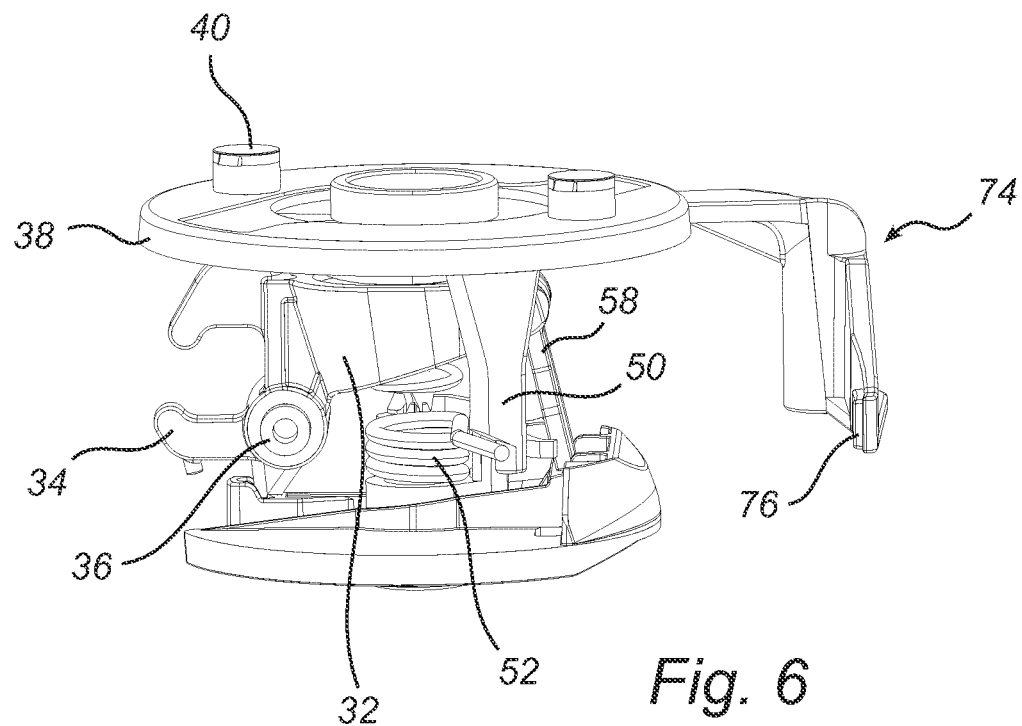
Figure 7:
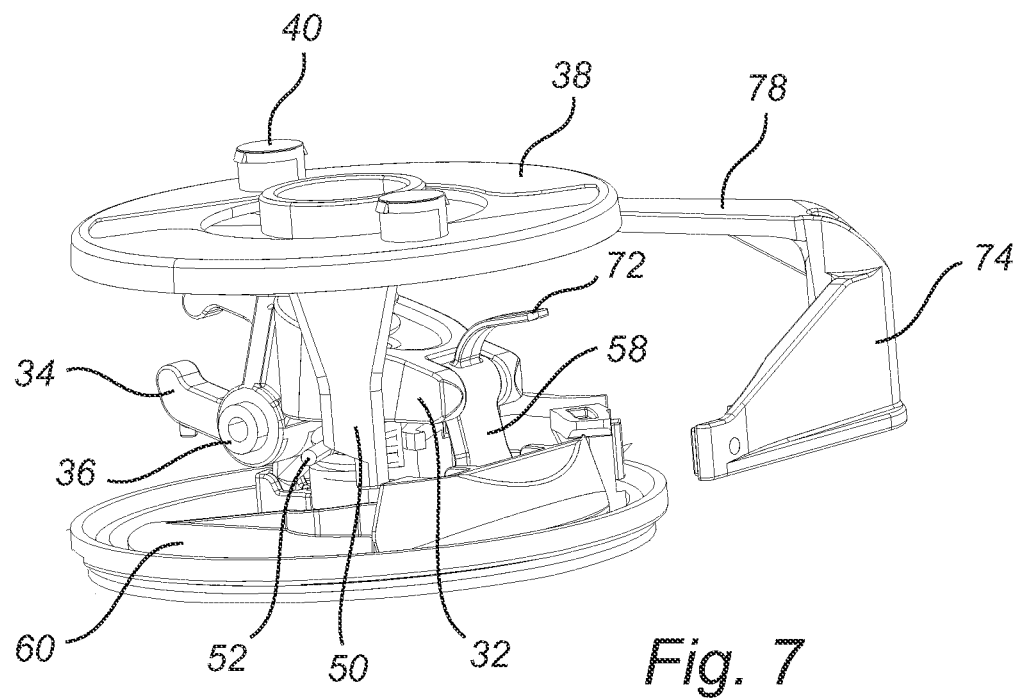
Figure 8:
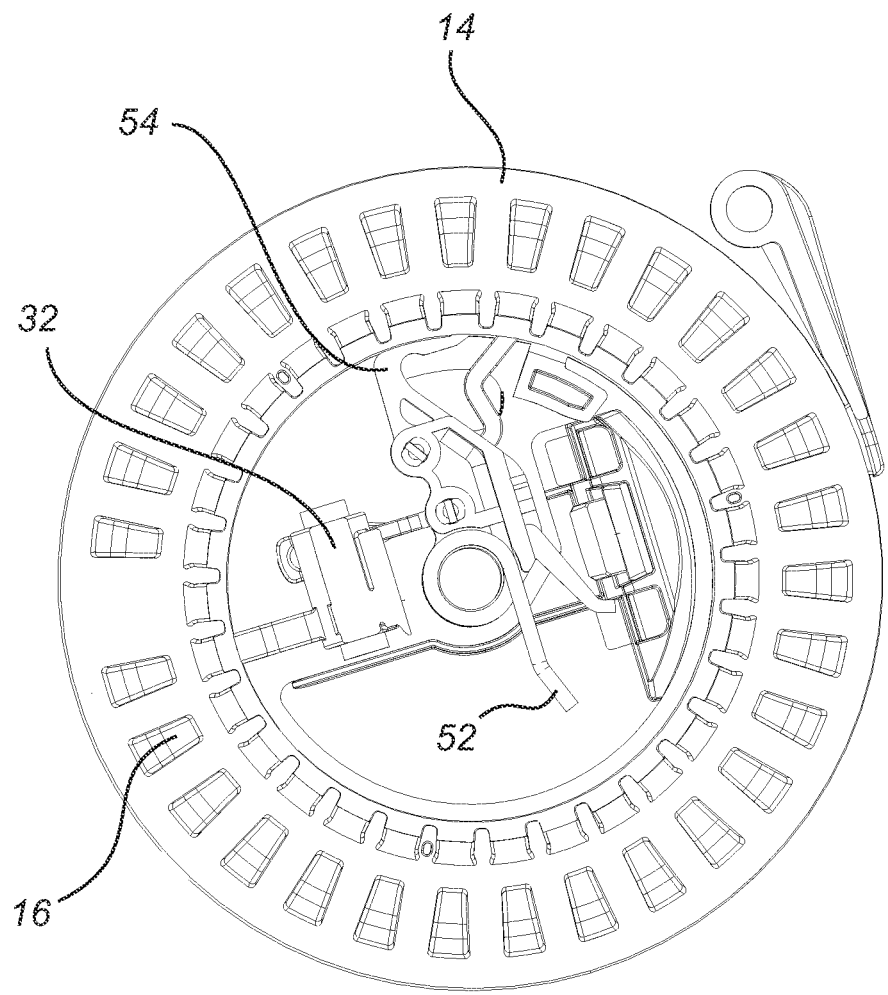

As illustrated in FIGS. 4, 6 and 7, the underside of the insert 38 is also provided with a projecting second force transmitting member 50 which is configured and adapted to engage an end of a torsion spring 52 located under the coil spring 46 and around the same post 48. The torsion spring 52 is connected to a drive member 54 for rotatingly advancing the cavities 16 by one increment at a time, so as to each time bring an unopened cavity in alignment with the mouthpiece 10. The drive member is best seen in FIGS. 8, 9, 10 and 11.

Figure 2:
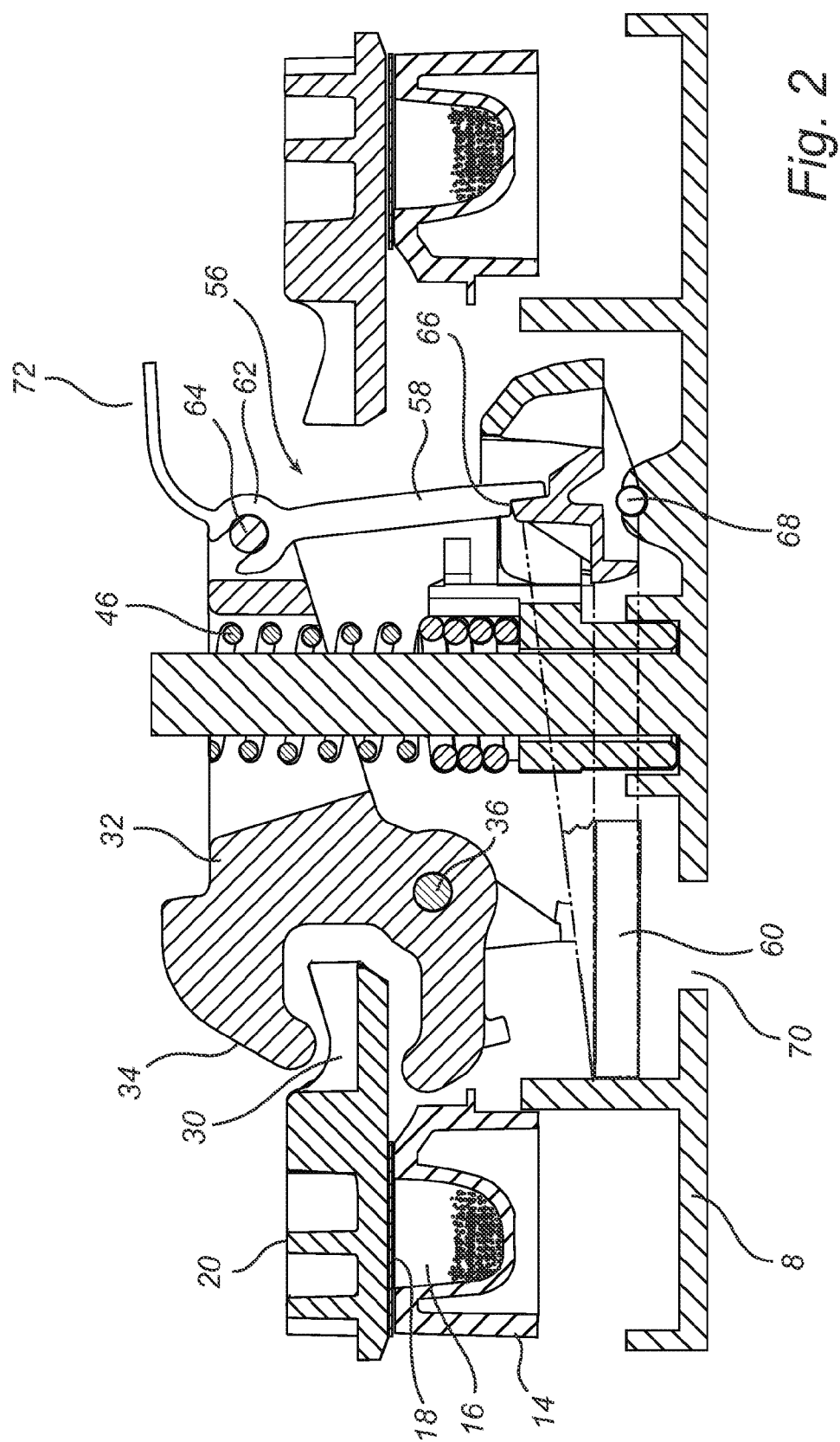
FIG. 2 is a cross-sectional view of selected details of the inhaler.

A latch 56 is provided to keep the actuator in the energized position, which is clearer from FIG. 2. The latch 56 comprises a first element in the form of an elongated prop 58 and a second element in the form of a flap 60. The elongated prop 58 has a first end portion 62 which is pivotable around a first horizontal axle 64 near that end of the actuator 32 which is located distally to the mouthpiece 10 (the jaws 34 being located proximally to the mouthpiece 10). The elongated prop 58 has a second end portion 66 adapted to be supported by the flap 60. The flap 60 is pivotable around a second horizontal axle 68. The flap covers a number of air inlets 70 (FIGS. 1-3) provided in the lower housing portion 8. Air is allowed to enter the inhaler 2 through said air inlets 70 when the user inhales through the mouthpiece 10 (outlet).

FIG. 2 is a cross-sectional view of selected details of the inhaler, wherein the inhaler is in a primed state, i.e. the actuator 32 is latched in an energized position. Thus, the jaws 34 of the actuator 32 have been lowered against the force of the coil spring 46 and now enclose the centrally projecting portion 30 of a separating element 20 aligned with the mouthpiece. The second end portion 66 of the elongated prop 58 is supported by a mating portion of the flap 60. The latch 56 comprising the prop 58 and the flap 60 is now in its first position, in which it latches the actuator 32 in the energized position. The latch 56 is biased towards its first position. More specifically, in this exemplified embodiment, the interface or contact point between the second end portion 66 of the elongated prop 58 and the flap 60 is located on the same side of the second horizontal axle 68 as is the portion of the flap 60 covering the air inlets 70 (in FIG. 2, the contact point between the elongated prop 58 and the flap is located left of the second horizontal axle 68). Thus, the centre of mass and the force on the flap 60 provided by the elongated prop 58 will be located left (in FIG. 2) of the pivot point provided by the second horizontal axle 68, thereby keeping the flap 60 in the illustrated lowered position. As long as the flap 60 remains still, the prop 58 is also prevented from moving, thereby keeping the actuator 32 latched in its energized position. The force exerted on the flap 60 is suitably adjusted to correspond to an airflow threshold which is exceedable by a user's inhalation. A position-keeping element 72 is provided at the first end portion 62 of the prop 58. From above, the position-keeping element 72 will be in contact with the disk-shaped insert 38 (FIG. 1). That contact will ensure that the prop 58 does not accidentally pivot around the first horizontal axle 64 in case the user should turn the inhaler in a different orientation (e.g. upside down) when closing the outlet cover 12. Thus, the flap 60 and prop 58 will be able to latch the actuator 32 even if a user holds the inhaler upside down when closing the outlet cover 12.

In at least one other embodiment, the illustrated position-keeping element 72 could rather function as a biasing spring element 72. In such an embodiment, the biasing spring element 72, would not just be in contact with the disk-shaped insert 38 (FIG. 1), but would actually be pressed downwardly by the disk-shaped insert 38. This force exerted on the biasing spring element 72 would have a levering effect about the first axle 64, urging the second end portion 66 of the prop 58 in a direction towards the jaws 34 and the mouthpiece (clockwise rotation in FIG. 2). This urging of the second end portion 66, which is in contact with a mating portion of the flap 60, would keep the flap 60 biased in the illustrated substantially horizontal lowered position. The biasing force transmitted from the biasing spring element 72 to the flap 60 would suitably be adjusted to correspond to an airflow threshold which is exceedable by a user's inhalation.

In another embodiment (not shown in the Figures), the element 72 could be replaced by a spring located on the insert 38. This could be a steel spring, for example, bearing on a small projection at the top of the prop 58 in order to bias it in essentially the same way as the element 72.

Figure 3:
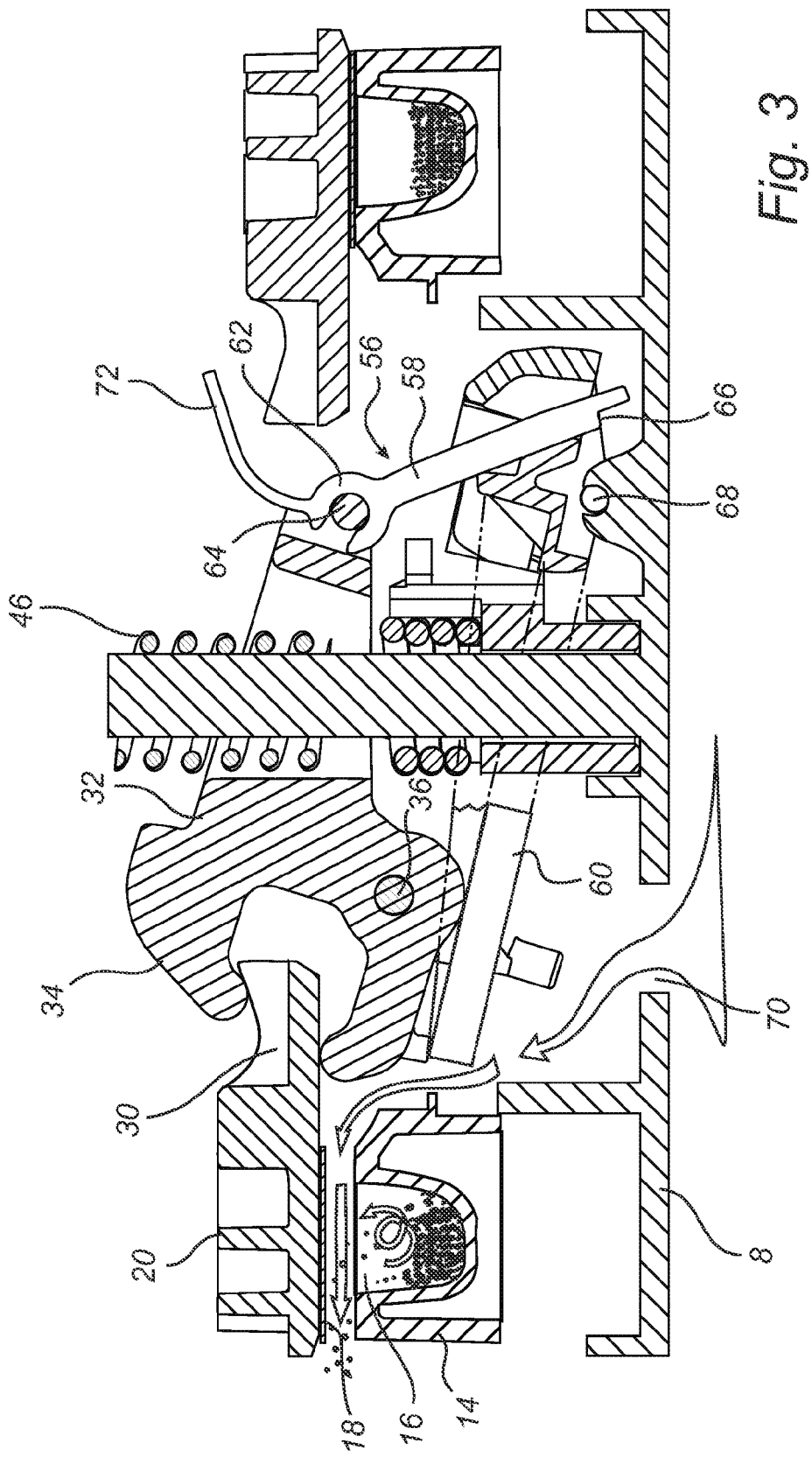
FIG. 3 illustrates, at the time of dispensing medicament from the inhaler, a cross-sectional view of selected details of the inhaler.

In order to administer a dose, the user inhales creating a sufficient airflow to raise the flap 60 against the biasing force. This is illustrated in FIG. 3. As the flap 60 is raised by the airflow and pivoted around the second axle 68 (clockwise in FIG. 3), the mating portion of the flap 60, being on the other side of the axle is lowered, whereby the second end portion 66 of the prop 58 loses its support. This will cause the prop 58 to pivot around the first axle 64 (anticlockwise in FIG. 3) and to "roll" off the mating portion of the flap 60. The latch 56 is now in its second position, in which it allows the actuator 32 to move to said unloaded position. Thus, the stored energy of the coil spring 46 will cause the now released actuator 32 to move. The actuator 32 will pivot around its axle 36 and the jaws 34 will be raised, whereby the engaged separating element 20 is lifted from the base 14. The foil portion 18 remains attached to the separating element 20, thus opening the medicament-containing cavity 16. FIG. 1 illustrates with dashed lines a separating element 20 being raised by the jaws 34 of the actuator 32.

It is realized that the design of the exemplified inhaler 2 provides for use of a phenomenon denoted as shear driven cavity principle during deaggregation of the powder in the cavity 16 and emptying of the powder therefrom. The shear driven cavity is a model for flow in a cavity where the upper boundary moves in a desired flow direction, and thus causes a rotation in the cavity. FIG. 2 illustrates a medicament powder-containing cavity 16 having a suitable headspace above the powder. In FIG. 3, the inhalation airflow passes by said headspace along a flats surface region, said flat surface region comprising the opening into the powder-containing cavity 16. The horizontal passing of the inhalation airflow leads to a build-up of an eddy air stream in the cavity 16 which causes powder to be deaggregated and emptied from the cavity 16. The cavity 16 is generally brick-shaped and the cavity opening has a rim where the sides of the cavity transcend into the flow passage flat surface region. Accordingly, the airflow, when passing the cavity in the flow passage, preferably flows in parallel with a plane coinciding with the rim of the cavity opening in the flow passage.

While the flap 60 may return to the lowered position after a dose is dispensed, the jaws 34 of the actuator 32 will remain in the unloaded position (see e.g. FIG. 7) until the user primes the inhaler for the next dose.

Although the priming of the inhaler 2 may be coupled to either the opening or closing of the outlet cover 12, in this example embodiment, it is assumed that closing of the outlet cover 12 primes the inhaler 2. Thus, when the user has inhaled a dose (FIGS. 3 and 7), he/she will close the outlet cover 12 to cover the mouthpiece 10 (FIG. 1). Although, the outlet cover 12 may be designed to form various travel paths, such as linear or stepwise paths, in this example embodiment the outlet cover 12 is rotated to cover the mouthpiece 10. During such closing of the outlet cover 12, the connected insert 38 with its force transmitting projecting member 50 and cam 44 will cause the jaws 34 of the actuator 32 to be lowered against the force of the coil spring 46 (FIG. 5) and the base 14 to be rotated, thus presenting an unopened next cavity 16 to the jaws 34. The insert 38 will also press the position-keeping element 72 of the prop 58, causing the latch 56 to return to its first position, whereby the actuator 32 is prevented from lifting its jaws 34. After that, when the user opens the outlet cover 12 in order to take another dose, the insert 38 will rotate the other way without affecting the latched and energized actuator 32. The inhaler 2 is now primed (triggered) and ready to be fired when the user breaths in through the mouthpiece 10, thereby enabling breath-triggered lifting of a foil portion 18 from a cavity 16.

In order to reduce the risk of latching the actuator 32 in the energized position without having aligned an unopened cavity 16, the latch 56 is prevented from returning to the first latching position before the next cavity is aligned with the mouthpiece 10. Also in order to reduce the risk of overindexing, i.e. passing an unopened cavity 16 past the mouthpiece 10 without opening the cavity 16, an indexing mechanism for sequentially aligning the cavities with the mouthpiece 10 is provided, wherein the indexing mechanism is adapted to align the next cavity 16 with the mouthpiece 10 after the actuator 32 has been moved from the unloaded position to the energized position.

Thus, in the illustrated example embodiment, after a dose has been dispensed, the user closes the outlet cover 12. As has been described above, the rotation of the outlet cover 12 causes the generally disk-shaped insert 38 to rotate. Through the rotation of the insert 38, the provided cam 44 will urge the actuator 32 (see FIG. 5) to move to its energized position. Thus, the jaws 34 of the actuator 32 will move from the raised unloaded position illustrated in FIGS. 3 and 7 to the lowered energized position illustrated in FIGS. 2 and 6.

Substantially simultaneously with the cam 44 urging the actuator 32, through the rotation of the insert 38, the projecting second force transmitting member 50 will urge the indexing mechanism to advance the next cavity 16 to be aligned with the mouthpiece 10. More particularly, as illustrated in FIG. 6, the projecting member 50 will energize the torsion spring 52 which is connected to the drive member 54 (see FIG. 8). The energized torsion spring 52 will urge the connected drive member 54 to rotate around the central axis provided by the post 48 (see FIG. 1) in order to engage the base 14 and to thereby cause the base 14 to rotate so as to bring the next cavity 16 aligned with the mouthpiece.

However, the force on the drive member 54 provided by the projecting member 50 via the torsion spring 52 is temporarily counteracted, at least until the actuator 32 has reached its energized position. If the jaws 34 of the actuator 32 would not be lowered before indexing, the separating element 20 next in turn would risk hitting the jaws 34 during the indexing.

Figure 5:
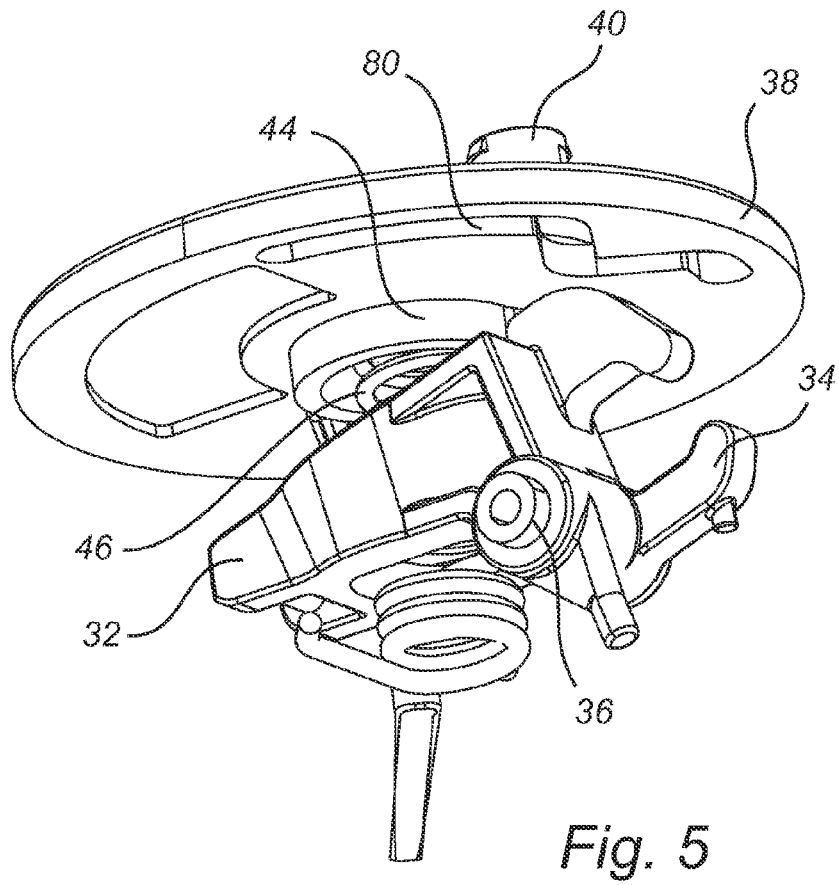
Figure 10:
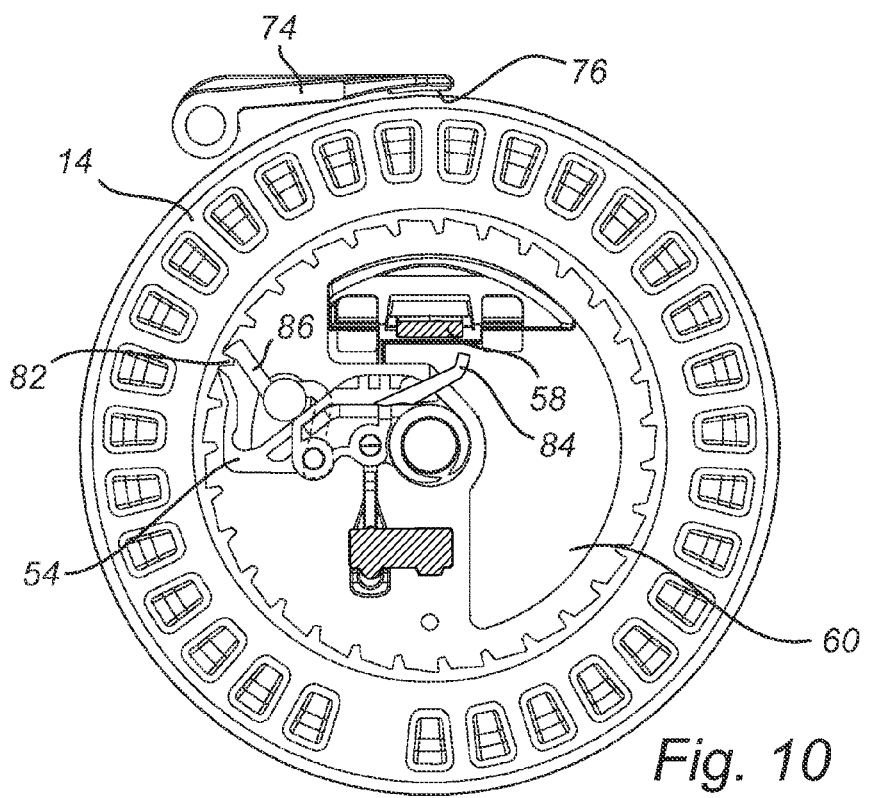
FIG. 10 is a cross-sectional view of selected details of the inhaler after indexing.
Figure 11:
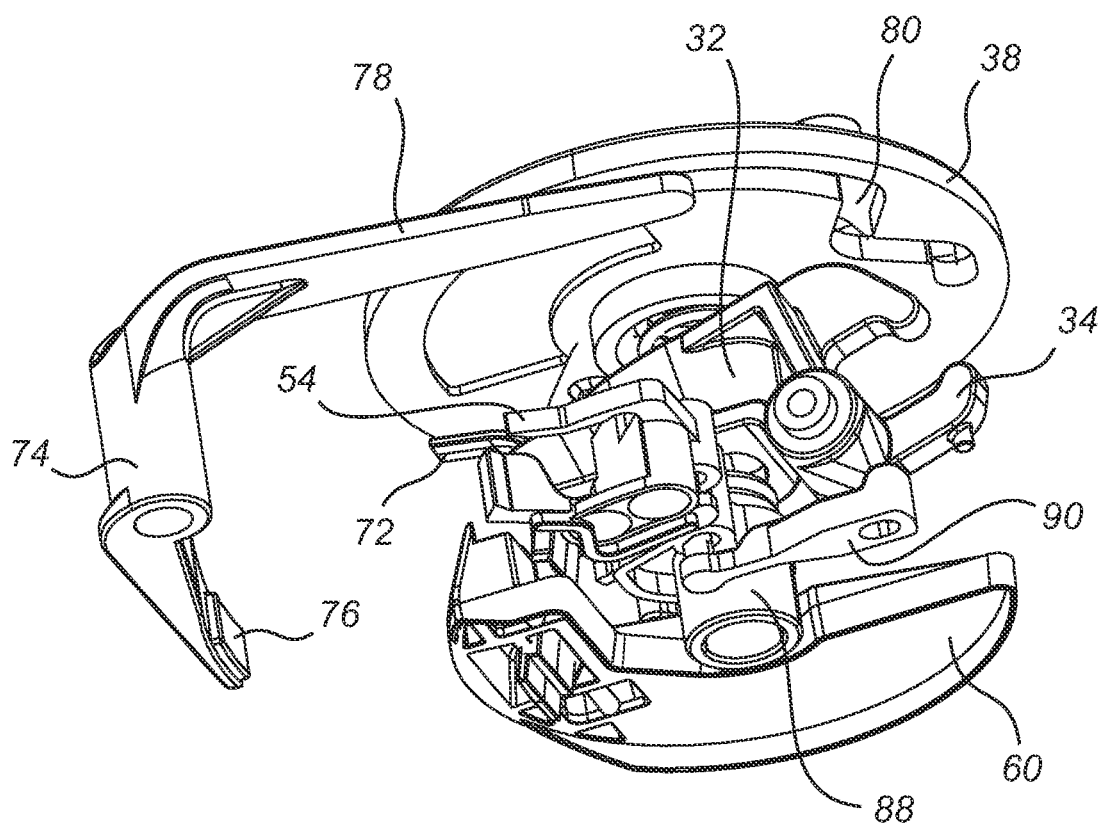

The counteracting member comprises a brake 74 adapted to prevent the compartments from moving. The brake 74 is attached to a lateral post 75 projecting from the lower housing portion 8 (see FIG. 1). The brake comprises a brake pad 76 which is pressed against the outer enveloping surface of the base 14 (see FIG. 9), thereby preventing the base 14 from rotating. The counteracting member also comprises a follower 78 (see FIGS. 1 and 11) which is connected to the brake 74 and which travels in a track 80 provided in the underside of the generally disk-shaped insert 38. The track 80 is best seen in FIGS. 4, 5 and 11, wherein FIG. 11 demonstrates how the follower 78 travels in the track 80. Thus, as the follower 78 travels in the track 80, it will follow an irregular path and when it reaches a point of release, the connected brake 74 lets go of the base 14 (FIG. 10). Now, the base 14 is allowed to be rotated by the drive member 54 which is urged by the torsion spring 52 as previously explained. Thus, the above exemplified mechanical sequencing assembly provides for alternate energizing of the opening mechanism (herein exemplified as the jawed actuator 32) and indexing of the compartments (herein exemplified as sealed cavities 16 in a base 14).

Figure 9:
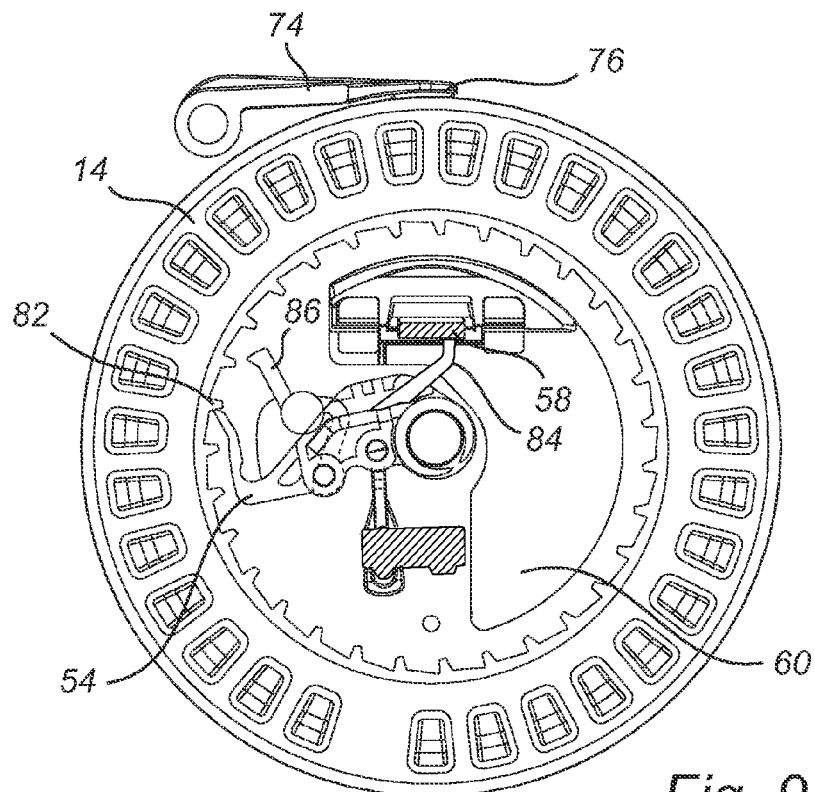
FIG. 9 is a cross-sectional view of selected details of the inhaler before indexing.

As illustrated in FIG. 9, before the brake 74 is released an end portion of the drive member 54 engages one of a plurality of teeth 82 in the base 14. An arm-shaped catch 84 is connected to the drive member 54 and may even be formed in one piece with the drive member 54. The catch 84 is in a preventing position, in which it prevents the first element (prop 58) of the latch 56 from becoming supported by the second element (flap 60) of the latch 56. Thus, in this state of the inhaler, the actuator cannot become latched in the energized position. Thus, the risk of re-firing from the same cavity 16 is reduced.

As the brake 74 is released, the drive member 54 will via the engaged tooth 82 rotate the base 14 one cavity-step. FIGS. 9 and 10 also illustrate a pawl 86 being pivotally mounted at a pivot point of the drive member (indicated with dashed lines). In FIG. 9, the pawl 86 is retracted, while in FIG. 10 the pawl 86 has been advanced to engage with a tooth 82, herein illustrated as engaged with the opposite side of the same tooth 82 that is pushed by the drive member 54. The pawl 86 prevents the drive member 54 from over-rotating the base 14, ensuring that the inhaler is indexed only one cavity-step at a time.

The drive member 54 and the catch 84 are connected to a common barrel 88 (best seen in FIG. 11) which swivels around the central post 48 (FIG. 1) projecting upwardly from the lower housing portion 8. As the drive member 54 rotates the base 14 the catch 84 will be removed from the preventing position, as illustrated in FIG. 10, thereby allowing the prop 58 to become supported by the flap 60 and latch the energized actuator. The inhaler is now primed.

As previously described, in particular in connection with FIGS. 2 and 3, when the user opens the outlet cover 12 and inhales through the mouthpiece 10, the flap 60 is raised so that the prop 58 comes off the flap 60, thereby unlatching the actuator 32. The actuator 32 being energized by the coil spring 46 will be raised so that the jaws 34 of the actuator 32 remove the separating element 20 and the foil portion 18 from the cavity 16 presently aligned with the mouthpiece 10. As can be seen in FIG. 11, a movable pulling arm 90 connects the drive member 54 with the actuator 32. As the actuator 32 and the jaws 34 are raised, the pulling arm 90 follows that motion whereby at the other end of the pulling arm 90, the drive member 54 will be pulled from the primed state shown in FIG. 10 to the fired state shown in FIG. 9. The catch 84 will consequently be moved back to its preventing position shown in FIG. 9. Next, when the user closes the outlet cover 12, the inhaler will once again become primed.

If the user, for some reason, does not close the outlet cover 12 enough, the follower 78 travelling in the track 80 will not reach its point of release, and consequently the brake 74 will not be released. This in turn means that there will be no indexing. Furthermore, although the actuator 32 is in its energized position, it will not become latched, as latching can only occur in connection with indexing, as explained above. Thus, if the user then opens the outlet cover 12, which has not been fully closed, the actuator 32 will simply move back to its unloaded position.

The herein discussed indexing mechanism, enables rotation of the base 14 to be limited to one direction. Thus, un-indexing may be prevented from occurring. This may be advantageous in connection with other types of opening mechanisms or separating elements.

It should be noted that in this application terms such as "upper", "lower", "above", "below" have been used for explanatory purposes to describe the internal relationship between elements of the inhaler, regardless of how the inhaler is oriented in the surrounding environment. For instance, in the exemplified embodiment in the drawings, the cavities 16 are regarded as being placed "below" the foil portions 18, while the separating elements 20 are regarded as being placed "above" the foil portions 18, regardless of how the inhaler 2 as a whole is held or turned by the user. Similarly, "horizontal" means a direction located in the plane of the foil portions 18 or any plane parallel to the plane of the foil portions 18, and "vertical" means any direction perpendicular to such planes.

Thus, a vertical line may intersect the cavities 16, the foil portion 18 and the separating elements 20.

Most components of the inhaler 2, such as the base 14, the separating elements 20, the actuator 32 and the latch 56 are suitably made of a plastic material, such as a polymer, however, other materials, such as metal or ceramic are conceivable alternatives.

The inhaler 2 may suitably comprise a structure that provides a moisture protection, such as e.g. a moisture absorbent sink as described in WO2006/000758, or any other appropriate alternative for including desiccant material.

In a further embodiment (not shown in the figures), the cover 12 could be replaced by a cover which extends over the majority of the housing and having an open configuration in which the mouthpiece is exposed and a closed configuration in which the mouthpiece as well as the majority of the housing is enclosed in the cover. The cover could have, formed on its internal surface, the cam surfaces which are in previous embodiments associated with the insert 38. An aperture in the housing would be provided through which some or all of the cam surfaces could project in order to engage with the corresponding parts of the mechanism inside the housing.

The invention claimed is:

1. An inhaler, comprising a base having at least one sealed cavity containing medicament, a foil portion comprising two sides, one side being attached to the sealing the cavity in an air-tight manner, a separating element which is attached to the other side of the foil portion for separating the foil portion from the cavity, an actuator which is engagable with the separating element, the actuator having an energized position in which it is biased towards an unloaded position, wherein during movement from the energized position to the unloaded position the actuator causes the separating element to be moved away from the cavity, and a latch having a first position, in which it latches the actuator in said energized position, and a second position, in which it allows the actuator to be in said unloaded position, wherein the latch is at least partly arranged in a flow path such that an inhalation flow through the flow path affects the latch to move from the first position to the second position.

2. The inhaler as claimed claim 1, wherein said actuator comprises a pivotable lever comprising an engagement portion for temporarily engaging the separating element, the engagement portion being nearer the cavity when in said energized position than when in said unloaded position.

3. The inhaler as claimed in claim 2, wherein the actuator comprises an energizable spring for providing said actuator in the energized position.

4. The inhaler as claimed in claim 3, comprising:
   an outlet, such as a mouthpiece or a nasal adapter, an outlet cover movable for alternatingly closing and opening the outlet, and
   a pusher connected to the outlet cover, wherein, upon one of said closing or opening movements of the outlet cover, the connected pusher moves to push the actuator from the unloaded position to the energized position.

5. The inhaler as claimed in claim 4, wherein the opening and closing movements of the outlet cover are rotational, wherein the pusher comprises a cam which converts the rotational movement of the outlet cover to a linear pushing force affecting the actuator.

6. The inhaler as claimed in claim 5, wherein the latch is biased towards its first position.

7. The inhaler as claimed in claim 6, wherein the latch comprises a first element and a second element, the first element being connected to the actuator, the second element having a supporting position, in which it immobilizes the first element, thereby preventing the actuator from moving to the unloaded position, and a non-supporting position, in which the first element is enabled to move, thereby allowing the biased actuator to move to the unloaded position, wherein the second element is movable to the non-supporting position in response to the inhalation flow.

8. The inhaler as claimed in claim 7, wherein the second element is biased towards its supporting position.

9. The inhaler as claimed in claim 8, wherein the first element comprises an elongated prop having a first end portion which is pivotable on an axis and a second end portion adapted to be supported by the second element.

10. The inhaler as claimed in claim 8, wherein the second element is pivotable on an axis, wherein in response to the inhalation flow the second element is pivoted to allow the prop to fall off its support.

11. The inhaler as claimed in claim 10, wherein said base comprises a rotatable disk provided with a circumferentially-oriented sequence of cavities, each cavity being sealed by a respective foil portion, each foil portion being attached to a respective separating element, wherein upon rotation of the disk the separating element next in turn is presented to the actuator.

12. The inhaler as claimed in claim 11, wherein the medicament powder contains an active ingredient selected from mometasone, ipratropium bromide, tiotropium and salts thereof, salemeterol, fluticasone propionate, beclomethasone dipropionate, reproterol, clenbuterol, rofleponide and salts, nedocromil, sodium cromoglycate, flunisolide, budesonide, formoterol fumarate dihydrate, terbutaline, terbutaline sulphate, salbutamol base and sulphate, fenoterol, 3-[2-(4-Hydroxy-2-oxo-3H-l,3-benzothiazol-7- yl)ethylamino]-N-[2-[2-(4-methylpheny)ethoxy]ethyl]propane-sulphonamide, hydrochloride, indacaterol, aclidinium bromide, N-[2-(Diethylamino)ethyl]-iV-(2-{[2-(4- hydroxy-2-oxo-2,3-dihydro-l, 3-benzothiazol- 7-yl)ethyl]amino}ethyl)-3-[2-(l-naphthy)ethoxy]propanamide or a pharmaceutically acceptable salt thereof (e.g. dihydrobromide); N-Cyclohexyl-N³-[2-(3-fluorophenyl)ethyl]-N-(2-{[2-(4-hydroxy-2-oxo-2,3-dihydro- 1,3-benzothiazol-7-yl)ethyl]amino}ethyl)-β-alaninamide or a pharmaceutically acceptable salt thereof (e.g. di-D-mandelate); a [2-(4-Chloro-benzyloxy)-ethyl]-[2-((R)- cyclohexyl-hydroxy-phenyl-methyl) -oxazol- 5-ylmethyl]-dimethyl-ammonium salt (e.g. hemi-naphthalene-l,5-disulfonate); a (i?)-l-[2-(4-Fluoro-phenyl)-ethyl]-3-((5)-2-phenyl- 2- piperidin-l-yl-propionyloxy)-l-azonia-bicyclo [2.2.2]octane salt (e.g. bromide or toluenesulfonate); or a combination of any two or more thereof.

13. A method of dispensing a medicament from an air-tight foil-sealed cavity using the inhaler of claim 1, comprising:
   providing an airflow through the inhaler to activate the opening of the sealed cavity, opening the sealed cavity in response to said airflow by removing at least that area of the foil which is in register with the cavity opening, and dispensing the medicament entrained by the airflow.

14. The method as claimed in claim 13, wherein the act of opening the sealed cavity comprises lifting the foil from the cavity.

15. The method as claimed in claim 14, wherein the inhaler comprises the features defined in any one of claims 2-12.

* * * * *

UNITED STATES PATENT AND TRADEMARK OFFICE
CERTIFICATE OF CORRECTION

PATENT NO. : 9,095,670 B2  
APPLICATION NO. : 13/129393  
DATED : August 4, 2015  
INVENTOR(S) : John Briant et al.

Page 1 of 1

It is certified that error appears in the above-identified patent and that said Letters Patent is hereby corrected as shown below:

In the claims  
Claim 12, col. 18, lines 34-36,  
"(4-Hydroxy-2-oxo-3H-l,3-benzothiazol-7-yl)ethylamino]-N-[2-[2-(4-methylpheny)"  
should read  
--(4-Hydroxy-2-oxo-3H-1,3-benzothiazol-7-yl)ethylamino]-N-[2-[2-(4-methylphenyl)--.

Claim 12, col. 18, lines 37-40,  
"N-[2-(Diethylamino)ethyl]-iV-(2-{[2-(4-hydroxy-2-oxo-2,3-dihydro-l,3-benzothiazol-7-yl)ethyl]amino}ethyl)-3-[2-(l-naphthy)ethoxy]propanamide"  
should read  
--N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide--.

Claim 12, col. 18, lines 42-43,  
"(4-hydroxy-2-oxo-2,3-dihydro-l,3-benzothiazol-7-yl)"  
should read  
--(4-hydroxy-2-oxo-2,3-dihydro-1,3-benzothiazol-7-yl)--.

Claim 12, col. 18, lines 48-49,  
"a (i?)-l-[2-(4-Fluoro-phenyl)-ethyl]-3-((5)-2-phenyl-2-piperidin-l-yl-propionyloxy)-l-azonia"  
should read  
--a (R)-1-[2-(4-Fluoro-phenyl)-ethyl]-3-((S)-2-phenyl-2-piperidin-1-yl-propionyloxy)-1-azonia--.

Signed and Sealed this  
First Day of March, 2016

Michelle K. Lee  
*Director of the United States Patent and Trademark Office*